Aug. 22, 1950 F. W. ANDERSON Plant Pat. 974
NECTARINE TREE
Filed Aug. 30, 1949
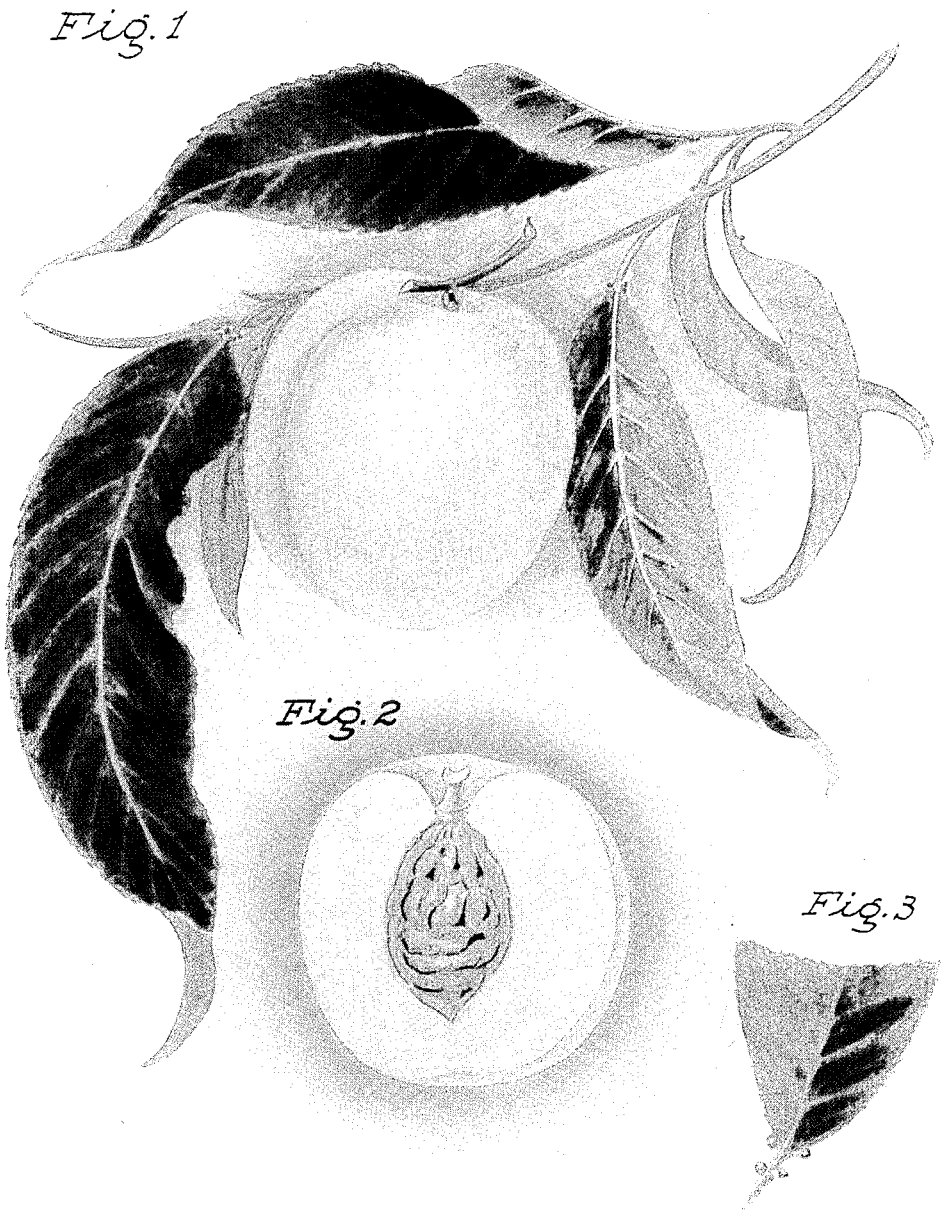
WITNESS
Addison J. Avery
INVENTOR
Frederic W. Anderson
Herbert Herbert
ATTYS Patented Aug. 22, 1950

Plant Pat. 974

UNITED STATES PATENT OFFICE

974

NECTARINE TREE

Frederic W. Anderson, Merced, Calif.

Application August 30, 1949, Serial No. 113,052

1 Claim. (Cl. 47—62)

The present invention relates in general to an improved nectarine tree, and in particular the invention is directed to, and it is the prime object to provide, a new and distinct variety of nectarine tree bearing yellow-fleshed freestone fruit having novel and commercially desirable characteristics.

The instant variety of nectarine tree is a result of a continuing effort by applicant to breed an improved variety of yellow-fleshed freestone nectarine.

The novel characteristics of the herein described nectarine tree are the large size, firm flesh, early ripening season, and superior shipping and eating qualities of the freestone fruit of such tree.

This new and distinct variety of nectarine tree was originated by applicant on his premises near Merced, California, and since its origination the variety has been successfully asexually propagated. An asexually reproduced nectarine of the variety has come into bearing and is found to retain all of the advantageous characteristics of the original tree and the fruit thereof.

In the original drawings:

Fig. 1 is a perspective view of the fruit in association with twigs and leaves of the variety.

Fig. 2 is a section taken axially of the fruit, and showing the stone.

Fig. 3 is a fragmentary sectional elevation of one of the leaves, showing particularly the glands.

More particularly the variety was originated and asexually reproduced as follows:

The variety is a second generation seedling of Kim nectarine (United States Plant Patent No. 173) crossed with the July Elberta peach (United States Plant Patent No. 15).

The first generation of this cross consisted of a group of yellow-fleshed freestone peaches, and the flowers of the latter were open-pollenated, and the pits of the resulting fruit were subsequently planted in a block for observation.

Of the resulting progeny about one quarter were yellow-fleshed nectarines, and the specific variety herein claimed was one of the earliest ripening of this group of nectarines. It first fruited in the summer of 1946 and was immediately recognized as being exceptional in its fruit characteristics.

The variety was top-worked on a bearing tree in applicant's orchard in the summer of 1946, and such top-workings initially fruited in 1948.

The fruit borne on the aforesaid top-workings, just as on the parent tree, was outstanding in size and appearance, and more than two weeks earlier in ripening than the three yellow-fleshed nectarines now being grown in, and shipped commercially from, California; viz: the Kim (United States Plant Patent No. 173); the Bim (United States Plant Patent No. 575); and the Le Grand (United States Plant Patent No. 549).

Referring now more specifically to the new and distinct variety of nectarine, the following is a detailed description, in outline, of such tree and its fruit:

Tree: Large size; medium strength; spreading; dense; vase formed. Productive; regular bearer.

Trunk: Medium size; medium texture.

Branches: Medium size; medium texture. Brown. *Lenticels*—medium number; medium size.

Leaves: Large—average length, 6½ inches; average width, 2 inches. Thick. Dark green.

*Margin.*—Crenate.

*Petiole.*—Medium length.

*Glands.*—Average four in number; alternate, medium size; globose. Positioned mostly on blade, occasionally on petiole. No stipules.

Flower buds: Medium size; plump.

Flowers: Large size; medium blooming period. First and full bloom with Elberta peach.

Fruit: Maturity when described—hard, July 5, 1948.

*Size.*—Large, uniform; average diameter axially, 2½''; average transverse in suture plane, 2¾''.

*Form.*—Uniform; symmetrical.

*Suture.*—A distinct line extending from base to beyond apex, with slight depression beyond pistil point.

*Ventral surface.*—Rounded slightly.

*Lips.*—Equal.

*Cavity.*—Rounded.

*Base.*—Rounded.

*Apex.*—Short.

Skin: Thick; tough; slight tendency to crack. Red. Down—wanting.

Flesh: Yellow.

*Surface of pit cavity.*—Pink.

*Amygadalin.*—Moderate.

*Juice.*—Moderate.

*Texture.*—Firm, meaty.

*Fibres.*—Few.

*Ripens.*—Evenly.

*Flavor.*—Vinous.

*Aroma.*—Distinct.

*Eating quality.*—Good to best.

Stone: Free; parts from flesh smoothly.

*Size.*—Medium. Average length, 1¼"; average breadth, $1\frac{1}{16}$"; average thickness, ½".

*Form.*—Oval.

*Base.*—Oblique.

*Hilum.*—Oval.

*Apex.*—Rounded.

*Sides.*—Equal.

*Color.*—Brown.

Keeping quality: Good.

Resistance to insects: Medium.

Resistance to diseases: Medium.

Use: Local, dessert, culinary, long distance shipping.

As compared to the present varieties of nectarines now grown in, and whose fruit is shipped commercially from, California the variety herein claimed bears fruit which ripens in the period between John Rivers and Grower varieties, both of which are white fleshed; the fruit of the instant variety being approximately one-third larger, and considerably more attractive in appearance.

As compared to the yellow fleshed varieties of nectarines being commercially grown, the present variety ripens slightly more than two weeks earlier than Kim (United States Plant Patent No. 173) or Bim (United States Plant Patent No. 575), and almost three weeks earlier than the Le Grand (United States Plant Patent No. 549); the latter ripening at approximately the same time as the white fleshed Quetta nectarine.

In 1948, the dates of first and last picking were July 3rd and July 13th, respectively.

In summary, the novel and characteristic features of the fruit of the claimed variety are:

1. Its earlier ripening period with respect to other commercial varieties of yellow fleshed nectarines.

2. Its larger size than the same.

3. Its superior shipping and eating qualities.

The tree and its fruit as herein described may vary in slight detail due to climatic and soil conditions under which the variety may be grown.

Having thus described my invention I claim:

A new and distinct variety of nectarine tree substantially as described and illustrated bearing yellow fleshed freestone fruit characterized by a ripening period between the white fleshed John Rivers and Grower varieties; approximately two weeks earlier than the yellow fleshed Kim or Bim varieties; and approximately three weeks earlier than the yellow fleshed Le Grand variety; its firm flesh; its relatively larger size; and its superior shipping and eating qualities.

FREDERIC W. ANDERSON.

No references cited.

Certificate of Correction

Plant Patent No. 974 August 22, 1950

FREDERIC W. ANDERSON

It is hereby certified that error appears in the printed specification of the above numbered patent requiring correction as follows:

Column 3, line 20, and column 4, line 21, for "Grower" read *Gower*;

and that the said Letters Patent should be read as corrected above, so that the same may conform to the record of the case in the Patent Office.

Signed and sealed this 12th day of December, A. D. 1950.

[SEAL]

THOMAS F. MURPHY,
*Assistant Commissioner of Patents.*